United States Patent [19]
Lee

[11] Patent Number: 5,915,845
[45] Date of Patent: Jun. 29, 1999

[54] WESTERN-STYLE TOILET BOWL SEAT EQUIPPED WITH FAR INFRARED LAMP

[76] Inventor: Doo-Pyung Lee, #130-606, Shinsigaji Apt., 901, Seoul, Rep. of Korea

[21] Appl. No.: 08/837,061

[22] Filed: Apr. 10, 1997

[30]    Foreign Application Priority Data

Oct. 15, 1996 [KR]   Rep. of Korea .................. 33847/1996

[51] Int. Cl.⁶ ................................................... A47K 13/00
[52] U.S. Cl. ..................................................... 4/237; 4/233
[58] Field of Search ................................ 4/233, 234, 237

[56]               References Cited

U.S. PATENT DOCUMENTS 2,458,019   7/1949   Niles ............................................ 4/233
3,045,096   7/1962   Clayton ....................................... 4/237

FOREIGN PATENT DOCUMENTS 0110261   4/1940   United Kingdom ....................... 4/233

*Primary Examiner*—Charles E. Phillips
*Attorney, Agent, or Firm*—Skjerven, Morrill, MacPherson, Franklin & Friel LLP; Alan H. MacPherson

[57] ABSTRACT

The present invention relates to a Western-style toilet bowl seat equipped with far infrared lamp.

The present invention comprises a lower seat of the toilet bowl 20 being mounted in an appropriate position of the top of a main body of the toilet bowl 10 and having a grille fastening part 21 and a socket fixing part 22 in an appropriate position, an upper seat of the toilet bowl 40 being placed on the top of said lower seat of the toilet bowl 20, and being mounted in opposition to a grille fastening part 41 and a socket fixing part 42, at least one or more first far infrared lamp 50 for emitting far infrared rays to the outside being mounted between the upper seat of the toilet bowl 40 and the lower seat of the toilet bowl 20, ON and OFF switches 80, 81 altanatively applying power to said far infrared lamp 50 and being mounted in an appropriate position of one side of the upper and lower seats of the toilet bowl 40, 20, at least one or more bracket 23 being mounted on one side of the upper and lower seats of the toilet bowl 40, 20 to fix the upper and lower seats of the toilet bowl 40, 20, a cover of the toilet bowl 60 being placed on the top of the upper seat of the toilet bowl and one end of the cover being fixed by a connection member 61 in an appropriate position of a bracket 23 so that the cover can be open and shut, and at least one or more fixing member 70 having one end being fixed in an appropriate position of the bracket 23 and the connection member 61, and the other end being fixed in an appropriate position of the main body of the toilet bowl 10.

6 Claims, 5 Drawing Sheets

WESTERN-STYLE TOILET BOWL SEAT EQUIPPED WITH FAR INFRARED LAMP

BACKGROUND OF THE INVENTION

1. Field of the Invention

The present invention relates to a Western-style toilet bowl seat equipped a far infrared lamp, and more particularly to the Western-style toilet bowl seat equipped with far infrared lamp in which electromagnetic waves radiating from the far infrared lamp are emitted to the vulva of a woman and the penis of a man while users are sitting on a toilet bowl for movements or urination to always maintain their genitals. The waves also are emitted to anus, to treat and prevent hemorrhoids by bettering the blood circulation at the region of the anus.

2. Description of the Related Art

A Western-style toilet bowl seat refers to a seat on which users are sitting on for movements or urination.

As such, Western-style toilet bowl seats for movements or urination having various functions have been the subject of many filed patent applications.

Namely, a toilet bowl seat for reducing the quantity of flush water, a toilet bowl seat equipped with a washing device, self-erection device for the toilet bowl seat, a bidet for washing the anus, etc., However, such a toilet bowl seat having the conventional construction mentioned above, did not have any apparatus which emits electromagnetic waves of far infrared rays (refers to the invisible wavelength of the rays of the sun, i.e. long electromagnetic waves; which are the essential rays during the growth of all the living things and is the mysterious light enabling to increase the combination with oxyhemoglobin and to activate the growth of cells together with the enlargement of minute blood vessels) to the genitals (more essential for women than for men) and the anus. As the result, the conventional toilet bowl seat had the drawback that users' genitals and anus could not be cleanly maintained all the time.

Further, if users sit on the toilet bowl for a long time, the structure of a human body impedes the circulation of the blood in the region of the anus, which leads to the attack of hemorrhoids. In this circumstances, the conventional toilet bowl seat had no means having technical constructions enabling to treat the hemorrhoids through the radiation of electromagnetic waves by using far infrared rays.

SUMMARY OF THE INVENTION

It is therefore an object of the present invention having the purpose of solving the conventional problems to provide a Western-style toilet bowl seat equipped with far infrared lamp in which electromagnetic waves radiating from a first far infrared lamp mounted in the marginal area of the toilet bowl seat are emitted to the vulva of a woman and the penis of a man while users are sitting on the toilet bowl for movements or urination to always maintain their genitals. Electromagnetic waves radiating from a second far infrared lamp mounted at the bottom of the lower seat of the toilet bowl are emitted to the anus, to treat and prevent hemorrhoids by bettering the blood circulation at the region of the anus.

To achieve such an object, the Western-style toilet bowl seat is equipped with a far infrared lamp according to the present invention which comprises a lower seat of the toilet bowl being mounted in an appropriate position of the top of a main body of the toilet bowl and having a grille fastening part and a socket fixing part in an appropriate position. An upper seat of the toilet bowl being placed on the top of the lower seat of the toilet bowl, and is mounted in opposition to the grille fastening part and the socket fixing. At least one or more first far infrared lamps for emitting far infrared rays to the outside are mounted between the upper seat of the toilet bowl and the lower seat of the toilet bowl, ON and OFF switches alternatively power to the far infrared lamp and are mounted in an appropriate position of one side of the upper and lower seats of the toilet bowl. At least one or more brackets are mounted on one side of the upper and lower seats of the toilet bowl to fix the upper and lower seats to the toilet bowl and, a cover of the toilet bowl is placed on the top of the upper seat of the toilet bowl. One end of the cover is fixed by a connection member in an appropriate position of the bracket so that the cover can be opened and shut, and at least one or more fixing members each having one end is fixed in an appropriate position of the bracket and the connection member, and the other end is fixed in an appropriate position of the main body of the toilet bowl.

BRIEF DESCRIPTION OF THE DRAWINGS

FIG. 4 is a view illustrating the operation state of the Western-style toilet bowl seat equipped with far infrared lamp according to the present invention, in which

DETAILED DESCRIPTION OF THE PREFERRED EMBODIMENT

Figure 1:
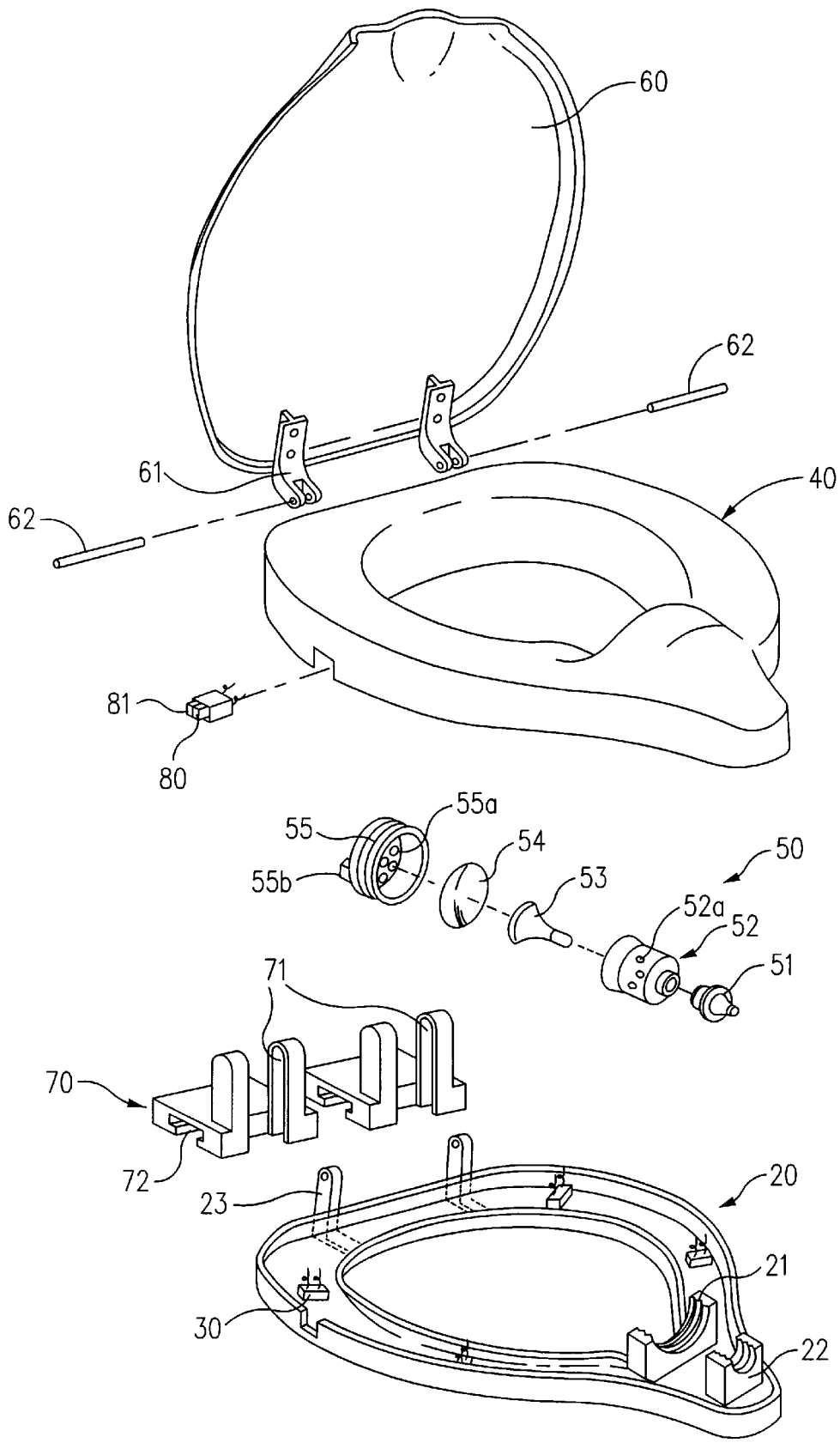
FIG. 1 is an exploded perspective view illustrating a Western-style toilet bowl seat equipped with the far infrared lamp according to the present invention.
Figure 2:
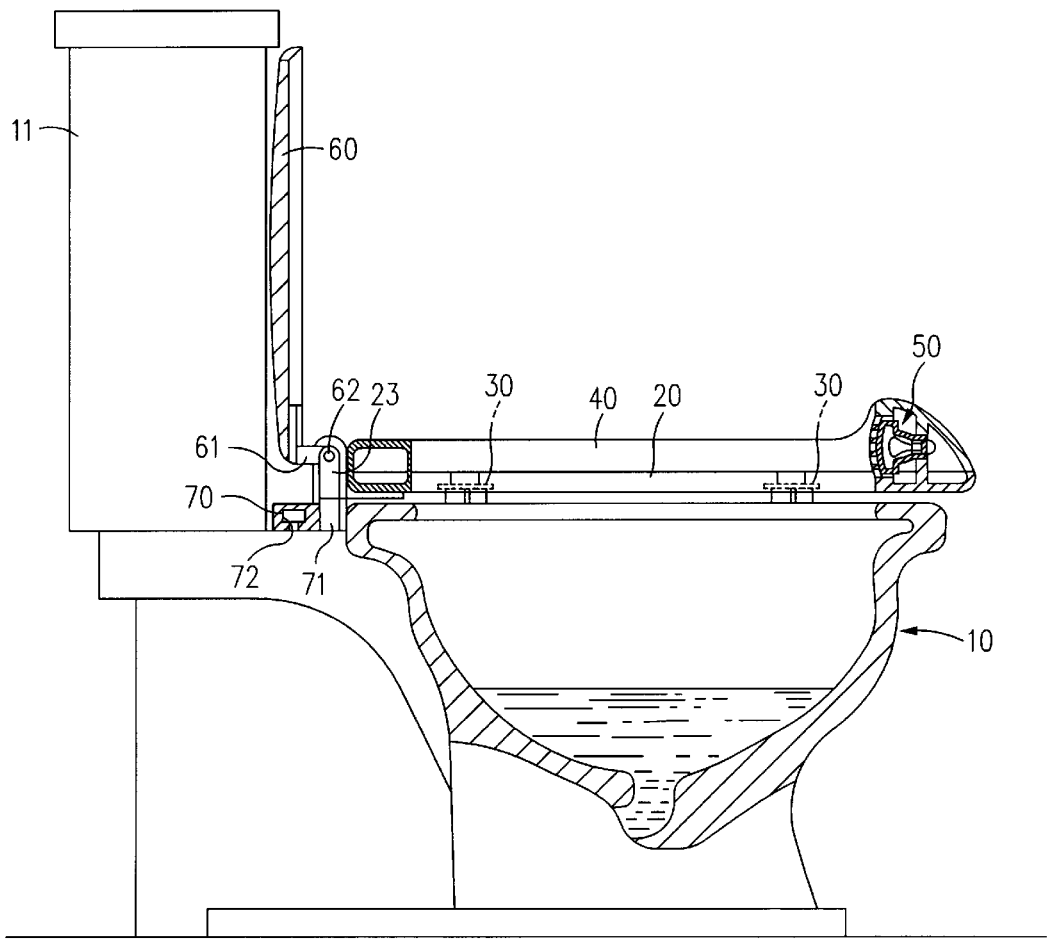
FIG. 2 is a section view illustrating the use state of the Western-style toilet bowl seat equipped with the far infrared lamp according to the present invention.
Figure 3:
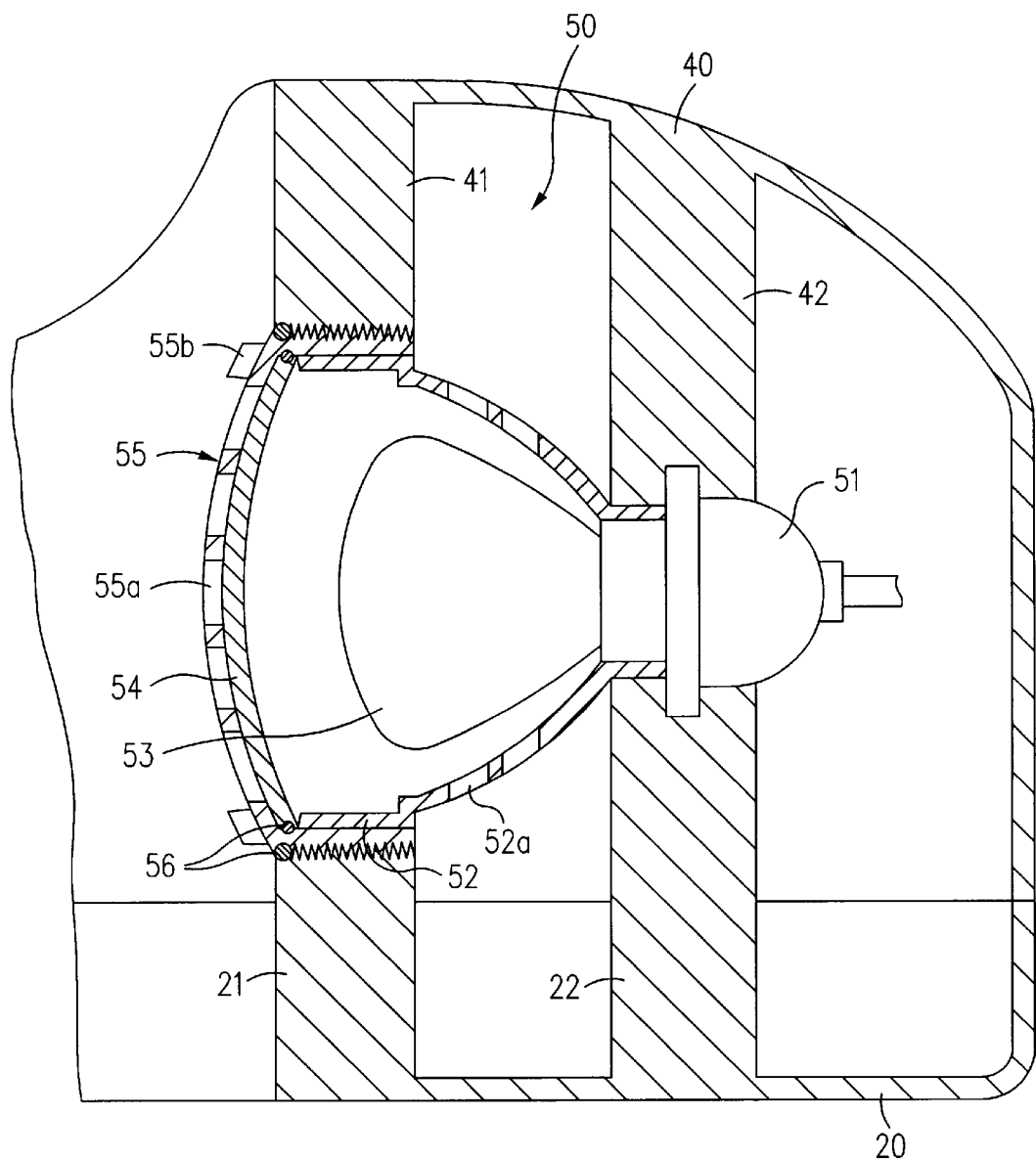
FIG. 3 is an enlarged sectional view of essential parts of the Western-style toilet bowl seat equipped with far infrared lamp according to the present invention.

The present invention will be described in more detail with reference to the accompanying drawings, in which like reference symbols indicate the same or similar elements components, wherein;

Referring to FIGS. 1 to 4, there is shown a Western-style toilet bowl seat equipped with a far infrared lamp wherein reference numeral 10 represents a main body of a toilet bowl. A toilet bowl seat 20, 40, extend from one side of the main body of the toilet bowl which includes a water tank 11 for storing and draining water.

Further, on the upper part of the main body of the toilet bowl 10 a lower seat 20 of the toilet bowl is placed, and in an appropriate position inside the lower seat of the toilet bowl 20 at least one or more load sensing means 30 is mounted. One end of the load sensing means is projectingly formed on the bottom of the lower seat of the toilet bowl at predetermined intervals.

Also, in an appropriate position of the lower seat of the toilet bowl a grille fastening part 21 and a socket fixing part 22 each having the screw thread of a semicircle are formed.

Further, on the upper part of the lower seat of the toilet bowl 20, an upper seat of the toilet bowl 40 is mounted, and on the upper seat 40 of the toilet bowl a grille fastening part 41 and a socket fixing part 42, each having a semicircular are formed.

Also, between the upper seat 40 of the toilet bowl and the lower seat 20 of the toilet bowl, at least one or more first far infrared lamps 50 emitting far infrared rays to the outside is mounted.

At the socket fixing parts 42, 22 formed on the lower and upper seats of the toilet bowl 20 and 40, respectively, a socket 51 is fixedly mounted, and on one side of the socket 51 a lamp 53 emitting far infrared rays is fixedly mounted. In the position adjacent to the outer circumference of lamp 53a radiating cap 52 having a plurality of holes 52a being formed at regular interval is mounted, and one end of the radiating cap 52 is fixedly mounted on the outer circumference of one end of the socket 51. At the grille fastening parts 41, 21 being formed on a upper and lower seats of the toilet bowl a grille 55 having the screw thread on the outer circumference is mounted, and in the grille 55 a plurality of holes 55a are formed at regular intervals, and in an appropriate position at least one or more projections 55b is formed projecting to the outside. Inside the grille 55 a lens 54 augmenting far infrared rays generated from the lamp 53 to the outside is mounted.

Further, between the outer circumference of the lens 54 and the inner circumference of the grille 55, and between the outer circumference of the grille 55 and the inner circumference of the grille fastening parts 21, 41 a packing 56 for preventing the infiltration of urine to the first far infrared lamp 50 is mounted.

Also, between the upper seat 40 of the toilet bowl and the lower seat 20 of the toilet bowl ON switch 80 and an OFF switch 81 for operating the first far infrared lamp 50 are mounted. The ON switch 80 and OFF switch 81 are mounted projectingly to the outside of the upper and lower seats 40, 20 of the toilet.

Further, on the upper seat of the toilet bowl a cover 60 for the toilet bowl is placed, and in an appropriate position of one side on the cover 60 at least one or more connection members 61 are mounted on one end. The other end of the connection member 61 is mounted in connection with a bracket 23 fixedly mounted in an appropriate position of the lower seat 20 of the toilet bowl and a hinge shaft 62. On both ends of the hinge shaft 62 a fixing member 70 is insertedly mounted, and on both ends of the fixing member 70 a guide groove 71 is formed through which the hinge shaft 62 is guided, and at the bottom of the fixing member 70 a fixing groove 72 is formed to be inserted into a bolt hind fastened in an appropriate position of the top of the main body of the toilet bowl 10.

Hereinafter, the operation and effects of the Western-style toilet bowl seat equipped with far infrared lamp according to the present invention having said construction will be described.

First, the hinge shaft 62 and the connection member 61 and the bracket 23 are interconnected, then on both ends of the hinge shaft 62 the hinge shaft 62 is mounted by inserting from the bottom of the guide groove 71 of the guide member 70 into the top thereof.

After the upper and lower seats 40, 20 of the toilet bowl are mounted on the main body of the toilet bowl 10, as such, users lift up the closed cover of the toilet bowl 60 by rotating it with the center of the hinge shaft 62 inserted into one end of the connection member 61.

After that, if users sit on the upper seat of the toilet bowl 40 and press ON switch 80 formed projectingly in an appropriate position on one side of the upper and lower seats of the toilet bowl with the application of power on the first far infrared lamp 50 far infrared rays are emitted to the outside, namely to the vulva in case of a woman and the penis in case of a man. As the result, the rays have an excellent effect on various diseases of a woman such as menstrual irregularity, feeling of cold, leukorrhea, etc. It also alleviates cytitis, lymph gland or insomnia or accelerates the circulation of the blood in the human body, and has effects on the regeneration of the skin tissue in prostatitis, herpes zoster, dermatitis, wet genital bursa which is an agony of a man only, etc.

Seeing the processes which far infrared rays are emitted from the first far infrared lamp 50, first, the socket 51 is securely fixed by the socket fixing parts 22, 42, at one end of the socket 51 the lamp 53 generating far infrared rays is mounted, and then far infrared rays are emitted to the outside. At the position adjacent to the outer circumference of the lamp 53 the radiation cap 52 having a plurality of holes 52a formed at regular intervals is mounted, in which the radiation cap 52 protects the lamp 53 and at the same time, prevents the communication of heat to the upper and lower seats of the toilet bowl consisting of synthetic resins.

As such, far infrared rays generated from the lamp 53 are emitted with the augmentation of far infrared rays by the lens 54, and the augmented far infrared rays are emitted to the outside through a plurality of holes 55a of the grille 55.

The grille 55 having the screw thread formed on the outer circumference is securely fastened to the grille fastening parts 21, 41, and the projection 55b formed on one end of the grille 55 is fastened or separated by easily rotating the grille by hand.

Each packing 56 formed between the lens 54 and the grille 55, and between the grille 55 and the grille fastening part 21, prevents the infiltration of urine to the inside of the first far infrared lamp 50.

With such operation, if users press the OFF switch 81, power does not apply to the first far infrared lamp 50, such that far infrared rays are not emitted any longer.

Figure 4A:
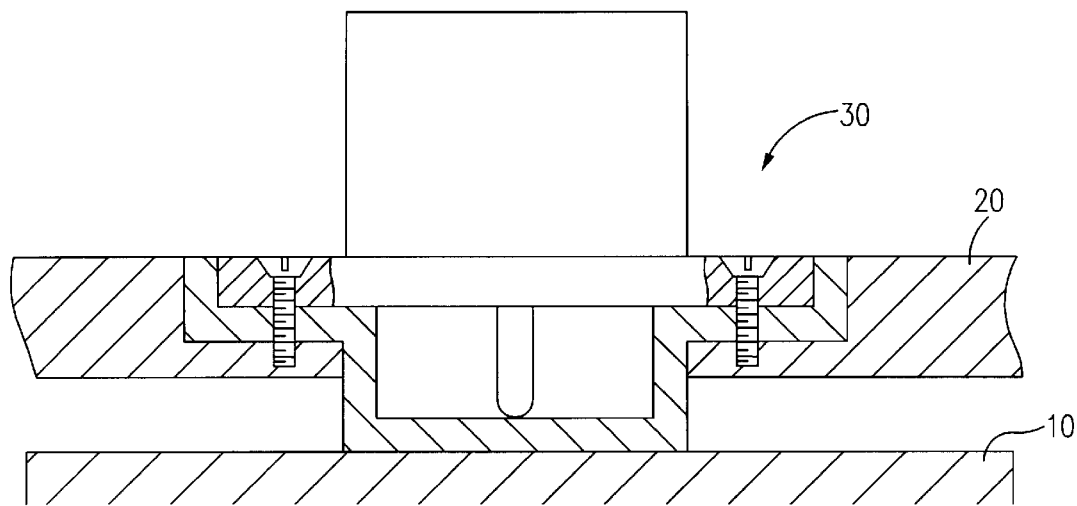
FIG. 4(A) is a view of the operation state of the present invention applied before the seat is pressed on and FIG. 4(B) is a view of the operation state of the present invention applied when the seat was pressed on and a load sensing means was operated.

According to the present invention, even under the state where the OFF switch 81 is pressed, power automatically applies to the first far infrared lamp 50, which enables the lamp to emit far infrared rays. Namely, FIG. 4(A) illustrates the state which power does not apply to the first far infrared lamp 50, as users did not sit on the seat of the toilet bowl and thus the load sensing means 30 could not sense a load. In such a state, the hinge shaft 62 is placed on the top of the guide groove 71 of the fixing member 70 as the upper and lower seats of the toilet bowl 40, 20.

Figure 4B:
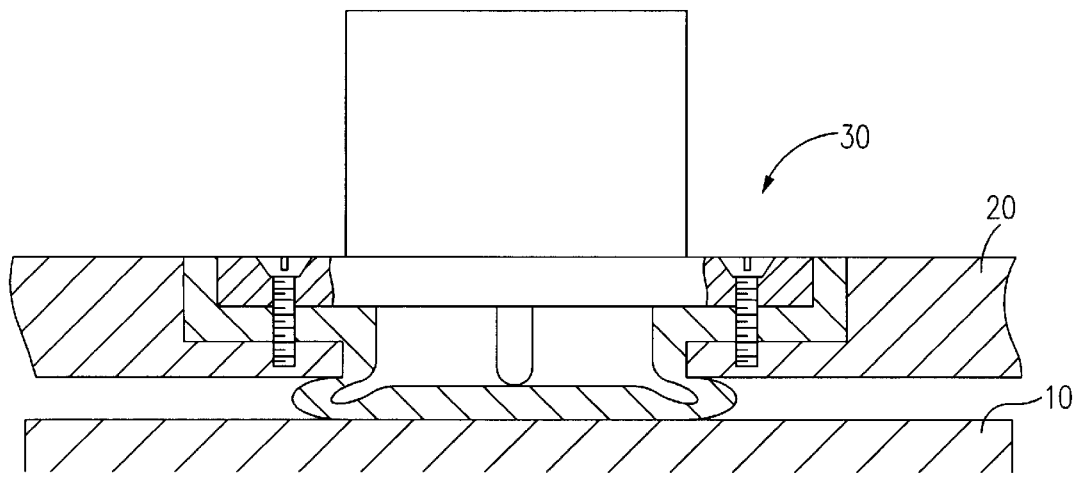

In such a state, if users sit on the seat 40 of the toilet bowl as shown in FIG. 4(B), the upper and lower seats of the toilet bowl 40, 20 are pressed with the weight of the users, at the same time the hinge shaft 62 is transferred to the bottom of the guide groove 71 of the fixing member 70, the load sensing means 30 comes in touch with the main body of the toilet bowl 10, which applies power to the first far infrared lamp 50, and when users have sat, automatically applies power to the first far infrared lamp 50, which enables the lamp to emit far infrared rays.

Figure 5:
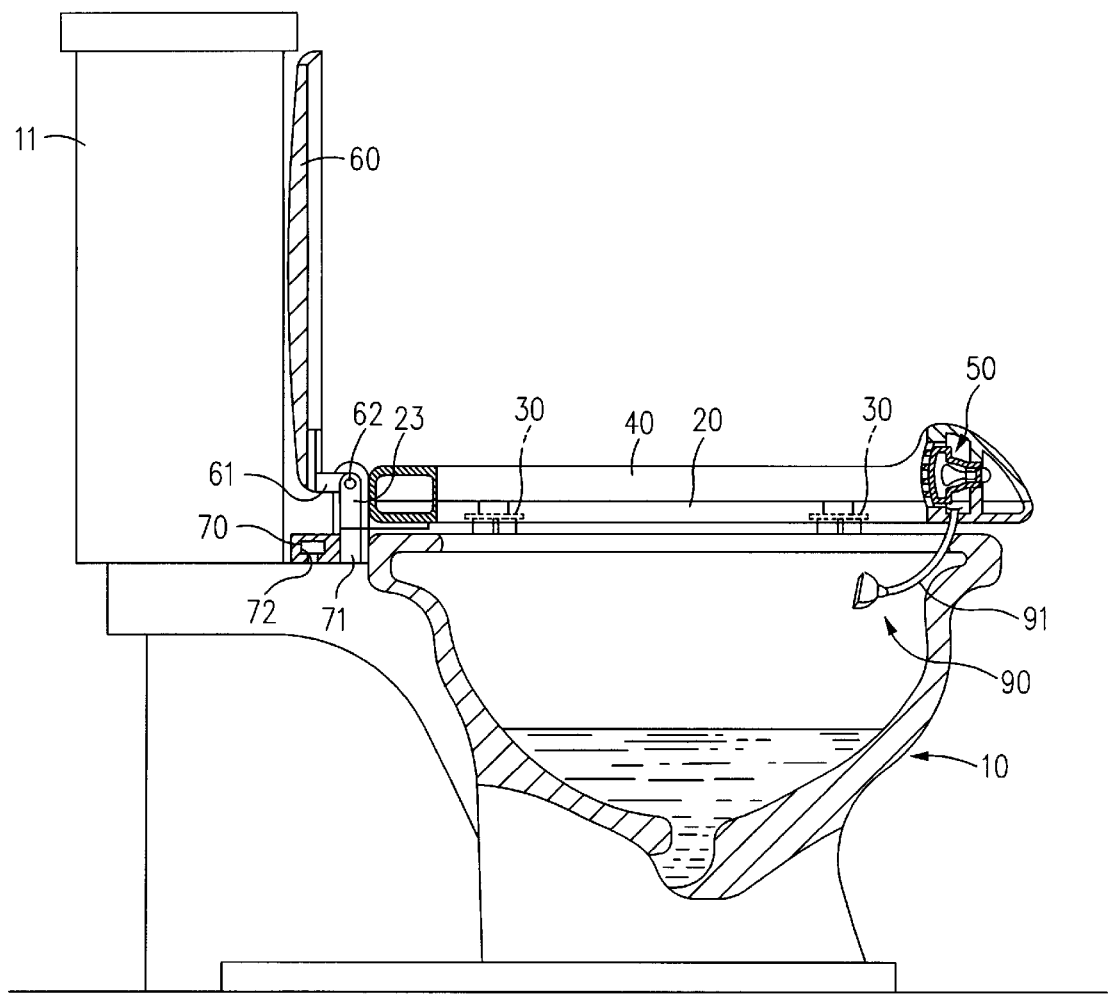
FIG. 5 is a sectional view illustrating another example of the Western-style toilet bowl seat equipped with a second infrared lamp according to the present invention.

Another example of the toilet bowl seat equipped with far infrared lamp according to the present invention is constructed as shown in FIG. 5. Namely, in an appropriate position of the lower seat of the toilet bowl a second far infrared lamp 90 is fixedly mounted on a flexible pipe 91 which is easily bendable. Besides that, all the construction in this example is the same as that of the above described construction.

The operation of the another example of the toilet bowl seat equipped with far infrared lamp according to the present invention is described hereinafter.

As described in the above, if users press ON switch 80, power applies to the second far infrared lamp 90, which enables to emit far infrared rays to the outside. Also, if users are seated on the upper seat of the toilet bowl 40, the load sensing means 30 is pressed with the weight of the user, which applies power to the second far infrared lamp 90, thereby emitting far infrared rays to the outside. As the flexible pipe 91 connected with the second far infrared lamp 90 is easily bendable, users can use the second far infrared lamp 90 facing toward the position as the users desire.

Effects of the Present Invention

As described in the above, electromagnetic waves radiating from the first far infrared lamp mounted on the marginal space of the seat of the toilet bowl are emitted to the vulva of a woman and the penis of a man while users are sitting on the seat for movements or urination. Accordingly, the waves various diseases of a woman and accelerates the circulation of the blood within the human body, and affect the regeneration of the skin tissue as well. Also, as electromagnetic waves radiating from the second far infrared lamp mounted on the bottom of the lower seat of the toilet bowl are emitted to the anus, the circulation of the blood at the region of the anus is improved, thereby treating and preventing hemorrhoids.

What is claimed is:

1. A Western-style toilet bowl and seat comprising:

a lower seat having a first end mounted on a top of a main body of the toilet bowl and having a first grille fastening part and a first socket fixing part on a second end of the lower seat.

an upper seat placed on a top of said lower seat said upper seat including a second grille fastening part and a second socket fixing part 42 opposed to said first fastening part and said first socket fixing part, respectively;

at least one far infrared lamp for emitting far infrared rays onto a user, said at least one lamp being mounted on said socket fixing parts between the upper seat and the lower seat;

ON and OFF switches alternatively applying or interrupting power to said far infrared lamp and being mounted on one side of the upper and lower seats;

at least one bracket mounted on one side of the upper and lower seats to fix the upper and lower seats to the toilet bowl;

a cover on the toilet bowl being movable onto a top of the upper seat, one end of the cover being fixed by a connection member on the at least one bracket so that the cover can be open and shut;

at least one fixing member having one end fixed on the at least one bracket and the connection member, and another end fixed on the main body of the toilet bowl.

2. A Western-style toilet bowl and seat as set forth in claim 1, wherein said first far infrared lamp comprises:

a socket fixed to the socket fixing parts;

a lamp bulb inserted into the socket and emitting far infrared rays;

a radiation cap having one end fixedly mounted on the socket, having a plurality of holes formed at regular intervals, and protecting the lamp bulb;

a grille fastened to the grille fastening parts and having a plurality of holes formed at regular intervals and at least one projection formed on one end; and a lens in an inner surface of the grille and augmenting far infrared rays generated from the lamp bulb.

3. A Western-style toilet bowl and seat as set forth in claim 1, further including at least one far infrared lamp mounted on a bottom front of the lower seat.

4. A Western-style toilet bowl and seat as set forth in claim 1, wherein said lower seat includes at least one load sensor, one end of said sensor projecting from a bottom of the lower seat of the toilet bowl and being pressed on the main body of the toilet bowl by the weight of a human body sitting on said upper seat to supply electrical power to said at least one far infrared lamp.

5. A toilet bowl and seat comprising:

a toilet bowl having a front portion, a rear portion and a central bowl top opening between said portions;

a seat pivotally movable with respect to the toilet bowl and having a rear hinged part and a seat front marginal area part facing the hinged part, said seat front marginal area including at least one far infrared lamp positioned to emit far infrared rays from said seat front marginal area toward the hinged part such that genitals of a human user sitting on said seat are treated by the far infrared rays; and further including a second far infrared lamp extending from said front marginal area into a position in the toilet bowl.

6. The toilet bowl and seat as set forth in claim 5 wherein said second far infrared lamp is connected to the front marginal area by a bendable flexible pipe for adjusting the second far infrared lamp position in the toilet bowl.

* * * * *